US009173634B2

(12) United States Patent  
Matsunaka et al.

(10) Patent No.: US 9,173,634 B2
(45) Date of Patent: Nov. 3, 2015

(54) FATTY TISSUE IMAGE DISPLAY DEVICE

(75) Inventors: Toshiyuki Matsunaka, Tokyo (JP); Hiromichi Horinaka, Osaka (JP); Hiroyasu Morikawa, Osaka (JP); Tomohiro Ogawa, Osaka (JP)

(73) Assignees: OSAKA PREFECTURE UNIVERSITY PUBLIC CORPORATION, Osaka (JP); ADVANTEST CORPORATION, Tokyo (JP)

( * ) Notice: Subject to any disclaimer, the term of this patent is extended or adjusted under 35 U.S.C. 154(b) by 335 days.

(21) Appl. No.: 13/637,999

(22) PCT Filed: Mar. 25, 2011

(86) PCT No.: PCT/JP2011/057395
§ 371 (c)(1),
(2), (4) Date: Sep. 28, 2012

(87) PCT Pub. No.: WO2011/125549
PCT Pub. Date: Oct. 13, 2011

(65) Prior Publication Data
US 2013/0018262 A1    Jan. 17, 2013

(30) Foreign Application Priority Data

Mar. 31, 2010 (JP) ................................. 2010-080293

(51) Int. Cl.
*A61B 8/08* (2006.01)
*A61B 5/00* (2006.01)
*A61B 8/14* (2006.01)

(52) U.S. Cl.
CPC ............. *A61B 8/0858* (2013.01); *A61B 5/4872* (2013.01); *A61B 8/5223* (2013.01); *A61B 8/14* (2013.01)

(58) Field of Classification Search
USPC ........................................................ 382/128
See application file for complete search history.

(56) References Cited

U.S. PATENT DOCUMENTS

| 5,485,561 | A  |   | 1/1996 | Iizuka et al. |
| 2003/0144592 | A1 | * | 7/2003 | Jeong et al. ............... 600/438 |

(Continued)

FOREIGN PATENT DOCUMENTS

| JP | 07-057073 A | 3/1995 |
| JP | 2001-145628 A | 5/2001 |

(Continued)

OTHER PUBLICATIONS

International Search Report PCT/JP2011/057395 dated Jun. 14, 2011 with English translation.

(Continued)

*Primary Examiner* — Parikha Mehta
(74) *Attorney, Agent, or Firm* — McDermott Will & Emery LLP

(57) ABSTRACT

A fatty tissue image display device includes a light source, an ultrasonic wave transmission/reception mechanism, an analysis unit which calculates a velocity change of ultrasonic waves after irradiation with a heating beam as compared to before irradiation with light, a display control unit which displays the distribution of the calculated velocity change of the ultrasonic waves, a designation unit which waits for the designation of a region of interest, a histogram calculation unit which, based on luminance information or color information within the designated region of interest, calculates the histograms of a fatty region showing a negative velocity change of the ultrasonic waves and a normal region showing a positive velocity change of the ultrasonic waves, and an index calculation unit which, from the calculated histograms of the fatty and normal regions, calculates a fatty change index that is an index of a proportion of fatty tissue.

5 Claims, 8 Drawing Sheets

(56) References Cited

U.S. PATENT DOCUMENTS

2004/0101086 A1    5/2004    Sabol et al.
2005/0078857 A1    4/2005    Park
2006/0020205 A1*   1/2006    Kamiyama .................. 600/437

FOREIGN PATENT DOCUMENTS

| JP | 2003-180679 A | 7/2003 |
| JP | 2004-174261 A | 6/2004 |
| JP | 2010-5271 A | 1/2010 |

OTHER PUBLICATIONS

Akira Yamada et al., "Performance evaluation of the visceral fat measurement using ultrasound tomography", Proceedings of Symposium on Ultrasonic Electronics, vol. 28, Nov. 14-16, 2007, pp. 339-340.

Satoshi Ishibashi et al., "Measurement of Fat Distribution Using Optically Assisted Ultrasonic Velocity Change Imaging", Optics & Photonics Japan 20098 Koen Yokoshu, Optical Society of Japan, Nov. 4, 200B, pp. 350-351.—English Abstract.

* cited by examiner

FATTY TISSUE IMAGE DISPLAY DEVICE

RELATED APPLICATIONS

This application is the U.S. National Phase under 35 U.S.C. §371 of International Application No. PCT/JP2011/057395, filed on Mar. 25, 2011, which in turn claims the benefit of Japanese Application No. 2010-080293, filed on Mar. 31, 2010, the disclosures of which Applications are incorporated by reference herein.

TECHNICAL FIELD

The present invention relates to a device for displaying an image of fatty tissue within a living body using data of a change in the velocity of the ultrasonic waves after irradiating the living body with a heating beam, such as of light, electromagnetic waves or ultrasonic waves.

BACKGROUND ART

Diagnostic imaging devices include roentgen devices for X-ray photographs, X-ray CT devices, PET devices, MRI devices and diagnostic ultrasonic devices, each of which has good points and bad points in terms of the cost for installing the device, the ability to diagnose a certain body area, the time for examination, whether or not there is a problem of exposure to radiation, and whether or not a chemical needs to be injected, and thus, they are used for different purposes of examination.

From among these diagnostic imaging devices, diagnostic ultrasonic devices and MRI devices are excellent with regards to safety because there are no problems of exposure to radiation. In addition, diagnostic ultrasonic devices are superior to MRI devices that also do not use radiation in the points that the cost of the device is low and the device is compact, which makes it portable.

Visceral obesity is cited as one risk factor of diseases from poor living habits, such as myocardial infarction, cerebral infarction, diabetes and fatty liver, and thus, those who have a high risk of getting a disease from poor living habits or obesity are diagnosed as having metabolic syndrome so that measures for preventing a disease can be taken from the point of view of preventive medicine. In order to diagnose whether a person has metabolic syndrome, it is necessary to check the amount of visceral fat.

In the case where a lump is found during mammary cancer screening, it is necessary to examine whether the lump is merely fat, which is a benign tumor, or a malignant tumor. In such a case, if whether the lump is made of fatty tissue can be easily detected, it can be judged to be benign or malignant using other references.

As described above, in some cases it is necessary to examine whether or not some tissues in a region of interest (ROI) within a living body are fatty tissue. In such a case, fatty tissue can be detected through image diagnosis using an X-ray CT device. However, the use of an X-ray CT device gives rise to the problem of exposing a subject to radiation.

Therefore, an examination for fatty tissue using ultrasonic wave tomography has been proposed as a safe imaging diagnostic method that does not cause a problem of exposure to radiation (see Non-Patent Document 1).

The velocity of the ultrasonic waves that propagate through muscles and internal organs (intestines, kidneys) is similar to the velocity of sound that propagates through water at a temperature of 37° C., and thus is generally 1500 m/sec or faster. In contrast, the velocity of the ultrasonic waves that propagate through fatty tissue is 1500 m/sec or slower, and therefore, the distribution of fat in the portion of a subject to be measured (abdominal region, for example) can be obtained from the data on the velocity of the ultrasonic waves in the case where it is possible to measure the velocity of the ultrasonic waves travelling through the tissues that form the abdominal region.

According to the ultrasonic wave tomography disclosed in the above document, the difference in the velocity of the sound that travels through different substances is used to estimate the amount of visceral fat by means of transmission measurement.

Meanwhile, a method for taking a tomographic image of the distribution of a change in the velocity of the ultrasonic waves in a target region through irradiation with light (tomographic image of the distribution of light absorption) where a conventional reflection type diagnostic ultrasonic device is used, a mechanism for irradiating a target region with light is provided, and a change in the velocity of an ultrasonic wave echo signal after irradiation with light, as compared to the time before irradiation with light, is calculated (see Patent Document 1).

The tomographic image of this change in the velocity of the ultrasonic waves (tomographic image of the distribution of light absorption) shows a change in the temperature in the target region due to the absorption of light for irradiation. That is to say, when a living body is irradiated with light, the distribution of the temperature within the living body depends on the light absorbing properties of the respective portions. The velocity of the ultrasonic waves that propagate through the living body changes depending on the temperature, and therefore, a change in the velocity of the ultrasonic wave echo signal after irradiation with light as compared to before irradiation with light can be found for each portion so that a tomographic image is gained, and thus, the distribution of the change in the velocity of the ultrasonic waves, the distribution of a change in the temperature or the distribution of light absorption can be displayed as tomographic images.

Thus, fatty tissue displaying devices with which fatty tissue of a subject can be displayed by means of a reflective type diagnostic ultrasonic device using the properties of the ultrasonic waves that pass through the fatty tissue and muscle/internal organ tissue and of which the velocity changes depending on the temperature have been proposed (see Patent Document 2).

In general, changes in the velocity of the ultrasonic waves depending on the temperature are compared as follows:
Water: +2 m/sec·° C.
Fat: −4 m/sec·° C.

That is to say, the velocity of the ultrasonic waves that travel through muscle or internal organs (intestines, kidneys) that include a large amount of water increases as the temperature rises, while the velocity of the ultrasonic waves that travel through the fat portions lowers, and thus, the polarity in the change of the velocity of the ultrasonic waves reverses. Therefore, an ultrasonic wave echo signal that has been received from the target region of a subject when not irradiated with near infrared rays and an ultrasonic wave echo signal that has been received from the target region after being irradiated with near infrared rays are received by an ultrasonic imaging probe fabricated with array transducers. Subsequently, data on the change in the velocity of the ultrasonic waves after irradiation with light in the target region is calculated on the basis of the ultrasonic wave echo signal before irradiation with light and the ultrasonic wave echo signal after irradiation with light. Then, the regions where a negative change in the velocity of the ultrasonic waves is exhibited after irradiation with light are identified as fatty regions from the calculated data on the change in the velocity of the ultrasonic waves.

FIGS. 13(a) to 13(c) are diagrams showing an example of tomographic images of fatty tissue described in Patent Document 2, where FIG. 13(a) is a diagram for illustrating a phantom that is a target object, FIG. 13(b) is a B mode image thereof, and FIG. 13(c) is an image showing the change in the velocity of the ultrasonic waves.

The main body of the phantom is made of an agar including intralipid that is a light scattering material and a piece of beef tallow including a carbon powder is buried in a portion of the phantom so as to be a fatty region. The carbon powder is provided in order to efficiently heat the piece of beef tallow when irradiated with light and functions as a contrast medium. A piece of agar including a carbon powder having approximately the same size as the piece of beef tallow is also buried as a reference for comparison.

This sample was irradiated with a laser beam with a wavelength of 809 nm for approximately 15 seconds (0.1 W/cm$^2$) so that data on a change in the velocity of the ultrasonic waves could be obtained. The regions where the velocity of the ultrasonic waves exhibited a negative change after irradiation with light are indicated by blue, and the other regions are indicated by red.

As a result, the region that includes the fatty region is indicated by blue so that the position can be clarified in the image of a change in the velocity of the ultrasonic waves in FIG. 13(c), though this can barely be distinguished in the B mode image in FIG. 13(b).

PRIOR ART DOCUMENTS

Patent Documents

Patent Document 1: Japanese Unexamined Patent Publication 2001-145628
Patent Document 2: Japanese Unexamined Patent Publication 2010-005271

Non-Patent Document

Non-Patent Document 1: Proceedings of Symposium on Ultrasonic Electronics, Vol. 28, (2007), pp. 339-340, 14-16 Nov. 2007

SUMMARY OF THE INVENTION

Problem to Be Solved by the Invention

The fatty tissue detecting device disclosed in Patent Document 2 can display the regions including fatty tissue in an image of a change in the velocity of the ultrasonic waves by clearly distinguishing them from the regions that do not include fat.

In addition, the basic structure of the above-described fatty tissue detecting device is the same as that of conventional diagnostic ultrasonic devices, and only a simple heat source and a function of analyzing the change in the velocity of the ultrasonic waves need to be added, and therefore, such a fatty tissue detecting device can be provided as an optional mechanism of a conventional diagnostic ultrasonic device that can be added afterwards.

However, it is not necessarily sufficient to simply specify the location of a region including fatty tissue for the actual diagnosis of a living body, but rather it is desirable for the proportion of the fatty tissue within the region to be objectively evaluated for diagnosis.

When it is diagnosed whether or not a liver is a fatty liver by taking an image of the liver, for example, an image of a change in the velocity of the ultrasonic waves can be used to specify the regions where there is fatty tissue within the liver. However, the proportion of the fatty tissue included in the specified regions (ratio of the number of cells of a fatty liver to that of a normal liver) cannot be measured, and therefore, it is difficult to objectively determine the degree to which the fatty liver progresses.

In the case of a fatty liver, normal liver cells and fatty liver cells are generally mixed (in a marbled state), and the fatty portions are not distributed to one place. Therefore, when the image of a change in the velocity of the ultrasonic waves shows the regions including fat on the screen using the difference in the luminance (namely, grayscale), only a mixture of the black and white regions is displayed. When normal liver cells are red and the fatty liver cells are blue in the display, the portions where there is fat are a mixture of blue and red. Though the locations of fatty liver portions can be specified in the image using the difference in the luminance or different colors as described above, it is difficult to objectively tell the degree to which the fatty liver progresses only from the image because the images of a fatty liver that has not progressed (low proportion of fat) and a fatty liver that has progressed (high proportion of fat) both show a mixture of black and white (or red and blue), which makes comparison difficult.

That is to say, when the image of a change in the velocity of the ultrasonic waves is visually observed, the fat content is qualitatively, subjectively and sensibly judged, of which the precision depends on the skill of the observer. Therefore, it has been desired to obtain a quantitative, objective, reasonable and stable diagnosis without depending on the skill of the observer. When the fat content of a subject is periodically measured, for example, it is desirable to confirm its chronological change using numerical values.

Thus, an object of the present invention is to provide a fatty tissue image display device capable of displaying an index indicating the degree of progress of fatty change using numerical values when fatty tissue, such as in a fatty liver, is displayed in an image of a change in the velocity of the ultrasonic waves.

Means for Solving Problem

In order to achieve the above-described object, the fatty tissue image display device according to the present invention is provided with: a heat source for emitting a heat beam that can heat a target region within a body; an ultrasonic wave transmission/reception mechanism which transmits an ultrasonic wave signal to the target region and receives an ultrasonic wave echo signal from the target region; an ultrasonic wave velocity change analyzing unit for calculating a change in the velocity of the ultrasonic waves at each point within the target region after irradiation with the heat beam on the basis of an ultrasonic wave echo signal received from the target region before irradiation with the heat beam and an ultrasonic wave echo signal received from the target region after irradiation with the heat beam; an ultrasonic wave velocity change image display control unit for displaying the distribution of a change in the velocity of the ultrasonic waves that has been calculated as a tomographic image on a screen of a display device by means of luminance information or color information; a region-of-interest designation unit that waits for part of the above-described tomographic image to be designated as a region of interest; a histogram calculation unit which, on the basis of luminance information or color information within the designated region of interest, calculates the histograms of a fatty region showing a negative change in the velocity of the ultrasonic waves and a normal region showing a positive change in the velocity of the ultrasonic waves; and a fatty change index calculation unit which, from the calculated histograms of the fatty region and the normal region, calculates a fatty change index that is an index of the proportion of fatty tissue.

Effects of the Invention

According to the present invention, a tomographic image of the distribution of a change in the velocity of the ultrasonic waves where the distribution of the change in the velocity of the ultrasonic waves is expressed by luminance information or color information is displayed on the screen so that it waits for the designation of a region of interest (ROI) by the observer. When the region of interest is designated, data on the change in the velocity of the ultrasonic waves for each point within the region of interest is divided into data on a positive change in the velocity of the ultrasonic waves and data on a negative change in the velocity of the ultrasonic waves through the calculations for finding a histogram. The data on a positive change in the velocity of the ultrasonic waves is handled for the normal region, and the data on a negative change in the velocity of the ultrasonic waves is handled for the fat region so that they are used to calculate a fatty change index, which is an index of the proportion of fatty tissue.

As a result, the calculated fatty change index is displayed so that the degree to which a fatty change progresses in the region of interest can be displayed numerically and quantitatively, and thus, the fat region can be objectively evaluated.

So far, fatty tissue has been displayed with a color on the screen so that the fat content can be easily seen. However, quantification has been difficult for the fatty tissue in a marbled state, though the existence of fat can be confirmed. The present invention makes it possible to numerically output the fat content even for fatty tissue in a marbled state, and therefore, objective diagnosis can be easily achieved. In particular, a subject can be periodically and repeatedly measured so that a chronological change in the fat content can be recognized as a change in the numeric value, and thus, the effectiveness can be seen in diagnosing metabolic syndrome.

Other Means for Solving the Problem and Effects

In the above-described invention, the region-of-interest designation unit may designate a region of interest so that the area of the designated region is constant.

Thus, a number of regions of interest where different locations are measured at different times can be compared so that the comparison in the degree of progress of a fatty change can be precise because regions of interest having the same area can be compared.

In the above-described invention, the fatty change index calculation unit may calculate the ratio of the area of the histogram of the fat region to that of the normal region as a fatty change index.

That is to say, when the area of the histogram exhibiting a positive change in the velocity is $S_1$ and the area of the histogram exhibiting a negative change in the velocity is $S_2$, which defines the fatty change index as $F=S_2/S_1$, the greater the ratio of fat is, the greater the gained index F is, and thus, the degree of progress can be easily expressed by numeric values.

In the above-described invention, the ultrasonic wave velocity change image display control unit may allow the luminance information or color information displayed on the screen to be ranked in multiple levels, and the fatty change index calculation unit may calculate a fatty change index that is weighted on the basis of the rank when the fatty change index is calculated.

It is possible for the difference in the luminance information or color information to indicate the degree to which a fatty change at each point has partially progressed, and therefore, the luminance information or the color information can be weighted on the calculation of the area ratio as a coefficient for expressing the degree of progress of a fatty change so that the degree of fatty change can be more precisely known.

In the above-described invention, a line-of-interest designation unit for designating the location of a line of interest on a tomographic image, and a line-of-interest graph display control unit for displaying as a graph the change in the velocity of the ultrasonic waves at each point along the designated line may further be provided.

The change in the velocity of the ultrasonic waves can be displayed as a graph along the designated line, and this can be referred to when the center position is searched before defining the location to be designated as a region of interest.

BEST MODE FOR CARRYING OUT THE INVENTION

In the following, the fatty tissue image display device according to one embodiment of the present invention is described in reference to the drawings. Here, a target portion is heated through irradiation with infrared rays by means of an infrared ray laser used as a heating means.

(Principle for Measurement of a Change in the Velocity of the ultrasonic waves)

First, the principle for measurement in an image of a change in the velocity of the ultrasonic waves displayed on the fatty tissue image display device is described below.

This data on the change in the velocity of the ultrasonic waves can be found from the following relationships.

Figure 14:
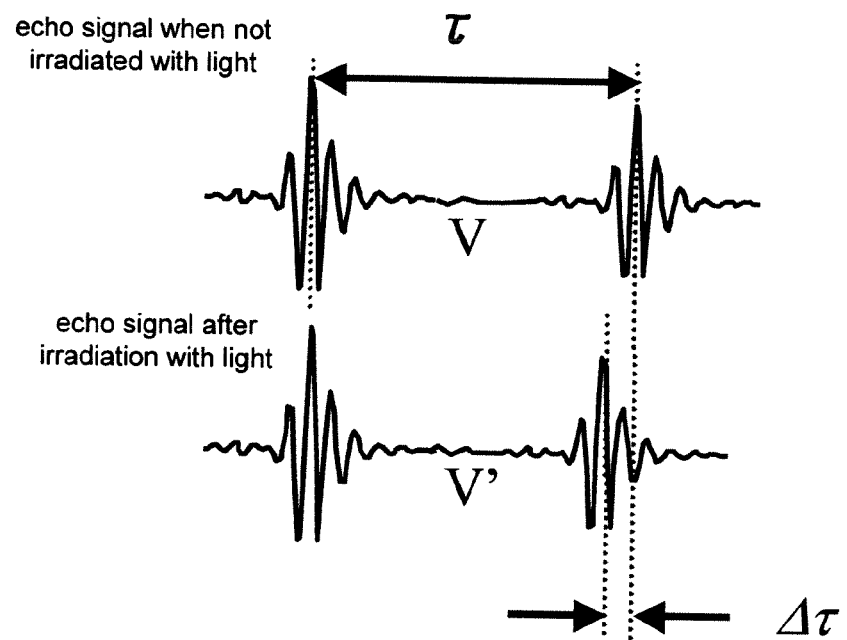
FIG. 14 is a schematic diagram showing an ultrasonic wave echo signal when not irradiated with light and an ultrasonic wave echo signal after irradiation with light.

FIG. 14 is a schematic diagram showing an ultrasonic wave echo signal when not irradiated with light and an ultrasonic wave echo signal after irradiation with light.

The velocity of the ultrasonic waves when not irradiated with light is V and the velocity of the ultrasonic waves after irradiation with light is V'. In addition, the time during which the ultrasonic wave signal propagates between certain borders when not irradiated with light is 1, and the time during which the ultrasonic wave signal propagates between the same borders (constant distance) after irradiation with light is $\tau-\Delta\tau$. That is to say, a change in the temperature causes such a shift that the pulse interval is shortened by $\Delta\tau$.

At this time, the following relationship is formed:

$$V\tau = V' \cdot (\tau - \Delta\tau) \quad (1)$$

Accordingly, the change in the velocity of the ultrasonic waves can be calculated in the following formula from the change in the period of time of the pulse interval between the two echo signals:

$$V'/V = \tau/(\tau - \Delta\tau) \quad (2)$$

Though the detailed description about the actual method for calculating the data on the change in the velocity of the ultrasonic waves is omitted, data on the change in the velocity of the ultrasonic waves at the respective points can be calculated by sorting the measured ultrasonic wave echo signals into many sections and calculating for each section the amount of shift of the wave form after irradiation with light as compared to before irradiation in accordance with a cross correlation method so that data on the change in the velocity of the ultrasonic waves for each section can be acquired.

As described above, when changes in the velocity of the ultrasonic waves in response to a change in the temperature are compared, water is +2 m/sec·° C. and fat is −4 m/sec·° C., and therefore, the velocity of the ultrasonic waves increases in muscle and internal organs (intestines, kidneys) that include a large amount of water as the temperature rises, while the velocity of the ultrasonic waves decreases in fat portions, and thus, the polarities of the change in the velocity of the ultrasonic waves are opposite.

From the calculated data on the change in the velocity of the ultrasonic waves, the regions that exhibit a negative change in the velocity of the ultrasonic waves after irradiation with light are detected as fat regions, and regions exhibiting a positive change are detected as normal regions.

That is to say, it is determined whether the ratio of the velocity of the ultrasonic waves found in the formula (2) is greater or smaller than 1, and in the case where it is smaller than 1, this region is determined as a fat region where the change in the velocity of the ultrasonic waves corresponding to a change in the temperature is negative.

(Structure of Fatty Tissue Image Display Device)

Figure 1:
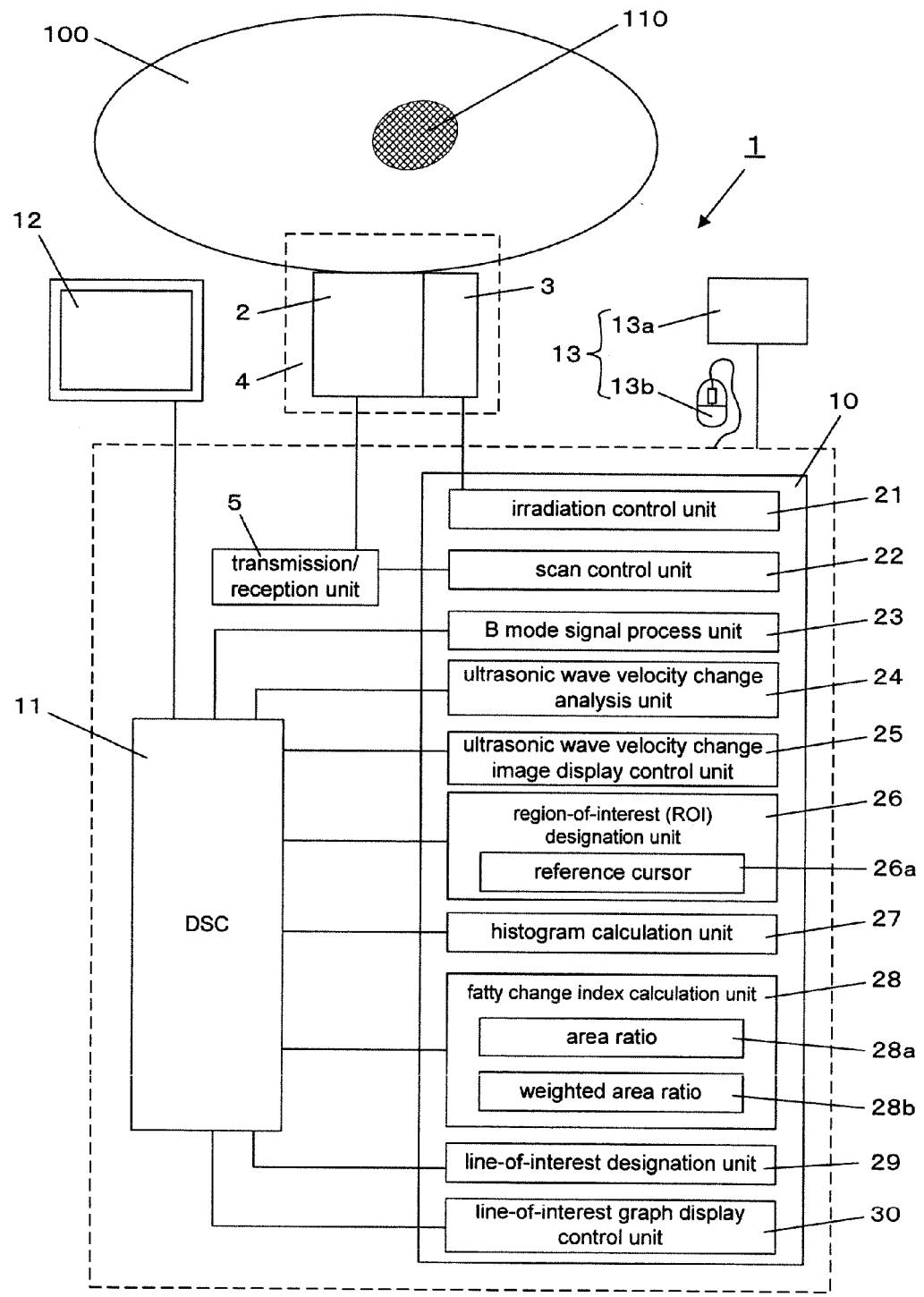
FIG. 1 is a block diagram showing the structure of the fatty tissue image display device according to one embodiment of the present invention.

Next, the structure of a fatty tissue image display device is described. FIG. 1 is a block diagram showing the structure of the fatty tissue image display device according to one embodiment of the present invention.

A fatty tissue image display device 1 is mainly provided with a probe 4 made of an array transducer type probe 2 and an infrared laser source 3, a transmission/reception unit 5 for driving the array transducer type probe 2, a control system 10, a digital scan converter (DSC) 11, a display device (liquid crystal panel) 12 and an input device 13 (keyboard 13a and mouse 13b).

The control system 10 is made of a CPU and a computer device having a memory and controls the respective units in the fatty tissue image display device 1, and at the same time arithmetically operates the gained measurement data when a software program stored in the memory is loaded so as to activate the control operation. For the sake of description, this control and arithmetic operation are divided into functional blocks: an irradiation control unit 21, a scan control unit 22, a B mode signal process unit 23, an ultrasonic wave velocity change analysis unit 24, an ultrasonic wave velocity change image display control unit 25, a region-of-interest designation unit 26, a histogram calculation unit 27, a fatty change index calculation unit 28, a line-of-interest designation unit 29 and a line-of-interest graph display control unit 30.

In the probe 4, the array transducer type probe 2 and the infrared laser source 3 are fixed together so as to be integrated so that a target portion 110 in a subject 100 can be irradiated with ultrasonic waves and a laser beam.

The array transducer type probe 2 has a number of oscillators aligned in one direction. Each oscillator is stimulated by a drive signal from the transmission/reception unit 5 so as to emit an ultrasonic wave signal and returns an ultrasonic wave echo signal from within the subject to the transmission/reception unit 5 in response to this ultrasonic wave signal.

The infrared laser source 3 emits infrared rays with a wavelength of 700 nm to 1000 nm as a heat source. Here, the wavelength of the light for irradiation or the type of light source can be changed so that the depth of the heated target portion from the surface can be adjusted.

The irradiation control unit 21 controls the irradiation of a subject with a laser beam from the laser source 3 having a preset laser output and a set interval of time. The range of change in the temperature of the target portion can be adjusted by adjusting the laser output and the interval of time.

The scan control unit 22 controls the time when the oscillators in the transmission/reception unit 5 are driven for control of transmitting and receiving an ultrasonic wave signal that becomes a number of scan lines (345, for example) to and from the array transducer type probe 2.

The irradiation control unit 21 and the scan control unit 22 are linked together for the control in order to obtain an image of a change in the velocity of the ultrasonic waves. That is to say, the scan control unit 22 carries out such control as to acquire an ultrasonic wave echo signal from the target portion before irradiation with a laser beam, and next, the irradiation control unit 22 heats the target portion through irradiation with a laser beam, and then, the scan control unit 22 again carries out such control as to acquire an ultrasonic wave echo signal from the target portion after irradiation with a laser beam.

A reception signal from the subject 100 is taken in through the transmission/reception unit 5 so as to be stored in the memory and is sent to the B mode signal process unit 23 and the ultrasonic wave velocity analysis unit 24 so as to be used to form a B mode image of ultrasonic waves or an image of a change in the velocity of the ultrasonic waves.

Figure 2:
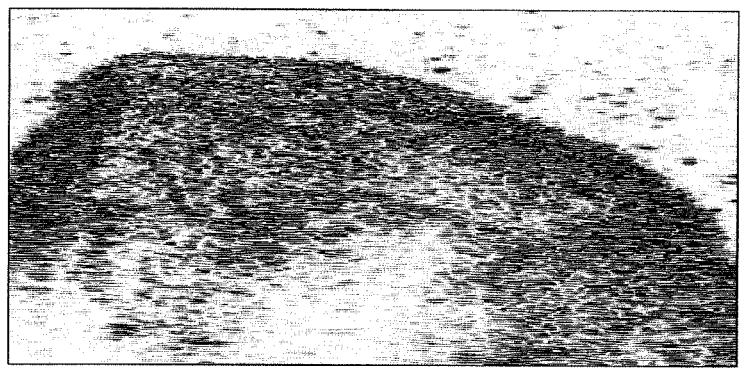
FIG. 2 is a photograph showing an example of a B mode image.

The B mode signal process unit 23 carries out a well-known B mode tomographic image forming process on the reception signal so that it is converted to luminance information, and thus forms a tomographic image within a beam scan range, which is written into the DSC 11. FIG. 2 is a photograph showing an example of a B mode image of chicken, which is displayed on the display device 12, formed of a reception signal (ultrasonic wave echo signal) of a great number of ultrasonic wave beams (345, for example). In this image, borders can be seen between adjacent tissues due to the brightness or darkness, but it is difficult to determine whether the tissues are fatty or normal.

The ultrasonic wave velocity change analysis unit 24 carries out such a process as to form an image of the distribution of the change in the velocity of the ultrasonic waves within a range scanned by an ultrasonic wave beam on the basis of the reception signals (ultrasonic wave echo signal) before and after irradiation with a laser beam. That is to say, an arithmetic operation for the formula (2) is carried out so that the data on the change in the velocity of the ultrasonic waves for each point within the scan range is calculated. The calculated data on the change in the velocity of the ultrasonic waves is sent to the ultrasonic wave velocity change image display control unit 25.

The ultrasonic wave velocity change image display control unit 25 ranks the data on the change in the velocity for each point depending on the size of the range of change (respectively ranks the positive and negative changes in the velocity into five levels, for example) and converts the data to color information (may be luminance information) corresponding to the rank. Thus, the portions corresponding to a positive change in the velocity and the portions corresponding to a negative change in the velocity are divided using color information.

In addition, the distribution of the change in the velocity of the ultrasonic waves shown by the color information (luminance information) for each point within the scan range is written into the DSC 11 as a tomographic image. The DSC 11 displays the tomographic image of the change in the velocity of the ultrasonic waves on the display device 12.

Figure 3:
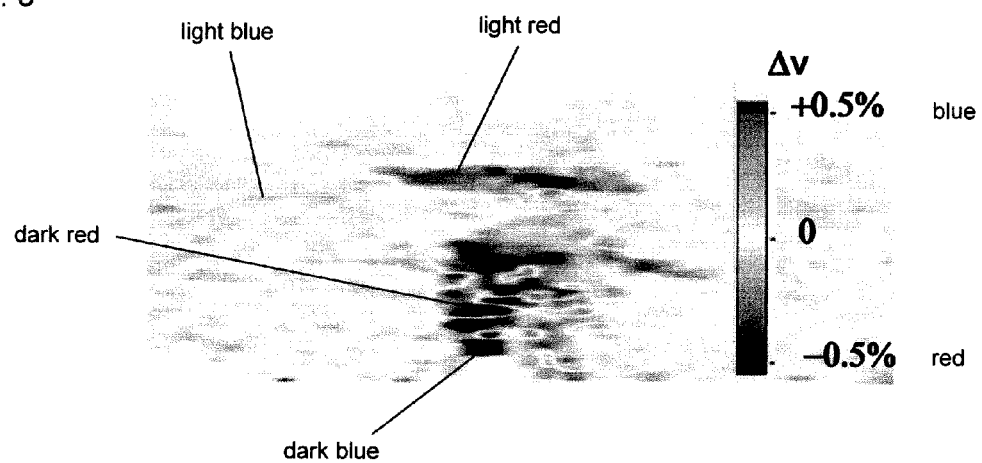
FIG. 3 is a photograph showing the image of a change in the velocity of the ultrasonic waves corresponding to the B mode image in FIG. 2.

For example, FIG. 3 is a photograph showing an image of the change in the velocity of the ultrasonic waves for the chicken of which the B mode image is shown in FIG. 2, which shows that the darker the blue is, the greater the velocity of the ultrasonic waves has shifted to the negative side, and the darker the red is, the greater the velocity of the ultrasonic waves has shifted to the positive side.

The region-of-interest designation unit 26 waits for an operator to input the designation of a partial region of the tomographic image displayed on the display device 12 as a region of interest (ROI) using the input device 13, and upon the reception of the input carries out such control that the color information (luminance information) corresponding to the designated region is sent to the histogram calculation unit 27. Concretely speaking, a message for encouraging an input for designating a region of interest is displayed ("Please designate a region of interest" is displayed, for example) at one end of the screen displaying the tomographic image of the change in the velocity of the ultrasonic waves, and thus, the operator is encouraged to designate a partial region on the screen with the cursor using the mouse 13b or the like. The designation may be encouraged by sound. It is preferable for the cursor for designation to be square, circular or rectangular.

Here, the area (reference area) of the region of interest designated by the cursor at this time may be stored in a memory so that the same reference cursor 26a can always be used for the designation. When the designated area is constant, that is to say, a region of interest is always designated as to have the same area, it is easier to compare different target portions or regions of interest measured at different times. If it is not necessary to make comparison with other measurement data, the system may be such that the operator can freely set the area designated by the cursor as a region of interest.

The histogram calculation unit 27 carries out an operation for calculating the histogram of fatty regions that show a negative change in the velocity of the ultrasonic waves and normal regions that show a positive change in the velocity of the ultrasonic waves on the basis of the color information or luminance information within the designated region of interest (ROI). Concretely speaking, pixels for a negative change in the velocity of the ultrasonic waves and pixels for a positive change are separated to calculate the histogram. Here, the positive changes in the velocity are separated into five levels and the negative changes in the velocity are separated into five levels to prepare a histogram.

The fatty change index calculation unit 28 calculates the ratio of the total number of pixels for a positive change in the velocity in any of the five levels to the total number of pixels for a negative change in the velocity in any of the five levels. In this case, the area ratio 28a of the normal regions to the fatty regions is calculated as a fatty change index F ($=S_2/S_1$).

Alternatively, pixels are weighted depending on the rank in any of the levels for positive and negative changes, and a weighted area ratio 28b is calculated in such a manner that the greater the change in the velocity is, the heavier the pixel for the rank is weighted.

In this case, the fatty change index $F=\Sigma(Li \cdot S_2)/\Sigma(Mi-S_1)$ is calculated when the weights for the positive and negative changes in the velocity ranked in the respective levels are Li and Mi (i=1 to 5).

Thus, the results of calculation of the fatty change index F can be displayed as a fatty change index value F on the display device 12.

In addition, the line-of-interest designation unit 29 waits for an operator to input the designation of the location of a line of particular interest (line of interest) on the tomographic image displayed on the display device 12, and upon the reception of the input samples the size of the change in the velocity of the ultrasonic waves at each point along the designated line for the control of sending the sampled size to the line-of-interest graph display control unit 30.

Concretely speaking, the above-described region-of-interest designation unit 26 displays a tomographic image showing the change in ultrasonic waves where an input of the designation of a region of interest is encouraged, and at this time, an optional message for designating a line of interest is displayed so that the operator is encouraged to designate a line on the screen using the mouse 13b or the like.

The line-of-interest graph display control unit 30 writes in the data on the change in the velocity of the ultrasonic waves at each point along the designated line of interest into the DSC 11 for the control of displaying a graph on the display device 12.

(Examples of Screen Display)

Figure 4:
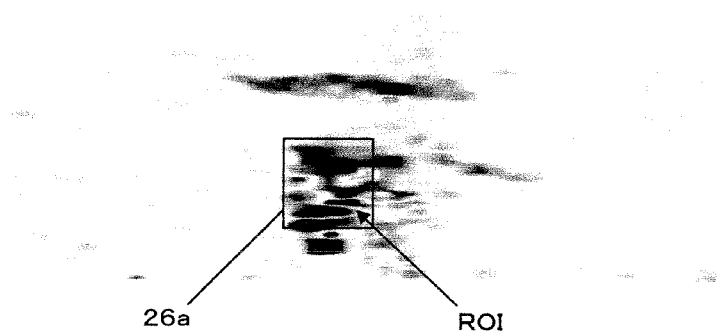
FIG. 4 is a photograph showing the screen for designating a region of interest (ROI)

Next, examples of the screen display displayed on the fatty tissue image display device 1 are described. FIG. 4 is a photograph showing a screen for designating a region of interest (ROI). A reference cursor 26a is displayed on the screen on which an image of a change in the velocity of the ultrasonic waves is displayed, and therefore, this is moved to a desired location so as to designate a region of interest (ROI). As a result, color information on each pixel within the designated region is sampled so that a histogram is calculated.

Actual fatty tissue in a living body is in a marbled state where normal regions and fatty regions are mixed. For the sake of simplicity of the description, the histograms that are displayed when the below-described various types of extreme phantoms are measured and the fatty change indices F calculated at that time are described.

(1) In the Case Where There Are Only Normal Regions

Figure 5:
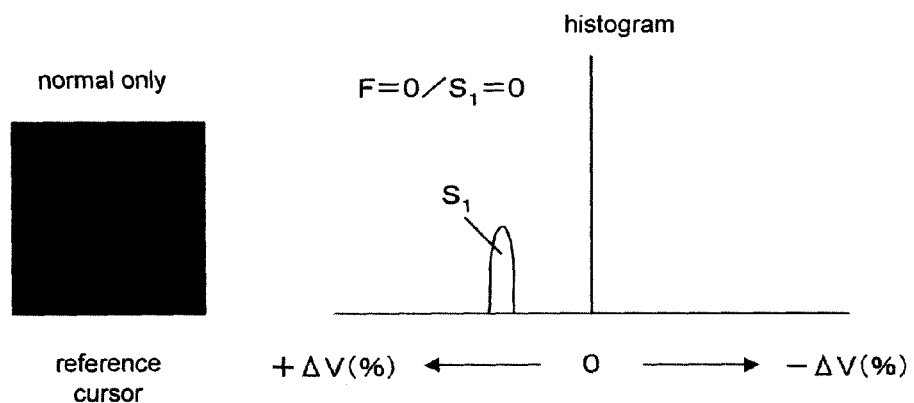
FIG. 5 is a diagram showing an example of a histogram in the case where a phantom is measured.

FIG. 5 shows a histogram in the case where a phantom, where the entirety within the region of interest (ROI) designated by the reference cursor consists of only normal regions that include no fat, is measured.

In this case, the histogram has an area $S_1$ where only a positive change in the velocity appears. The fatty change index F ($=S_2/S_1$) is 0 since $S_2$ is 0.

(2) In the Case where there are Only Fatty Regions

Figure 6:
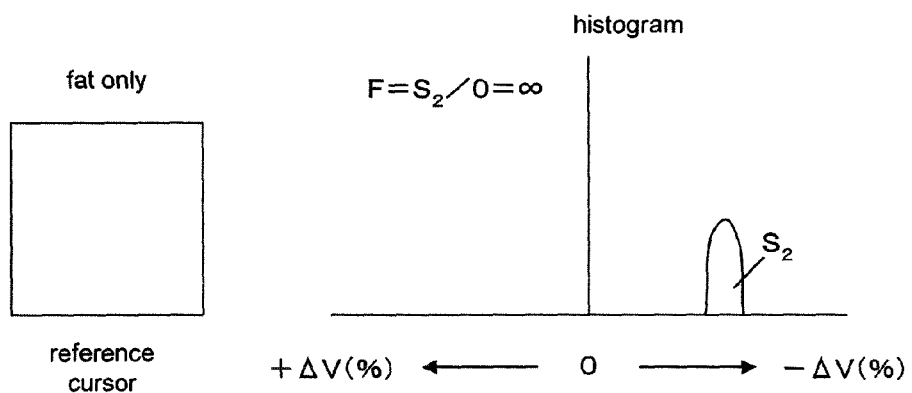
FIG. 6 is a diagram showing another example of a histogram in the case where a phantom is measured.

FIG. 6 shows a histogram in the case where a phantom, where the entirety within the region of interest (ROI) designated by the reference cursor consists of only fatty regions, is measured.

In this case, the histogram has an area S2 where only a negative change in the velocity appears. The fatty change index F ($=S_2/S_1$) is infinite ($\infty$) since $S_1$ is 0.

Figure 7:
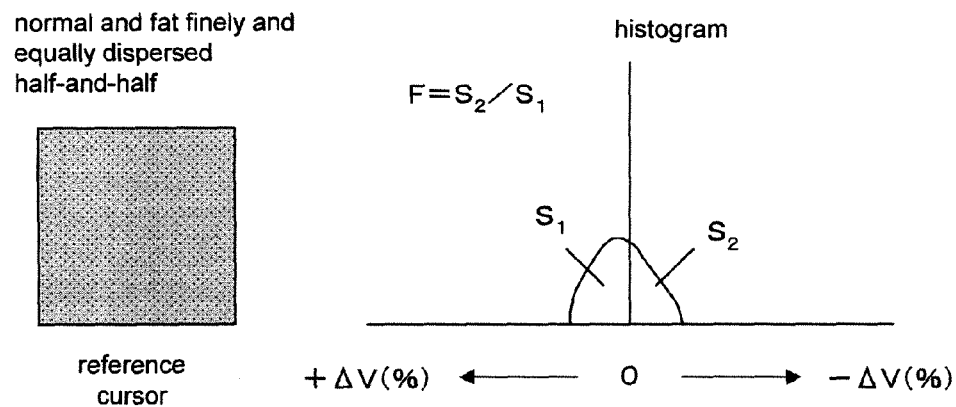
FIG. 7 is a diagram showing still another example of a histogram in the case where a phantom is measured.

(3) In the Case Where Normal Regions and Fatty Regions Are Finely and Uniformly Dispersed Half-and-Half FIG. 7 shows a histogram in the case where a phantom, where fatty regions and normal regions are finely mixed within the region of interest (ROI) designated by the reference cursor, is measured.

In this case, the histogram has an area $S_1$ and an area $S_2$ in the vicinity of the point where the change in the velocity is 0 where a positive change in the velocity and a negative change in the velocity appear almost half-and-half. The fatty change index F ($=S_2/S_1$) has a value close to 1.

Figure 8:
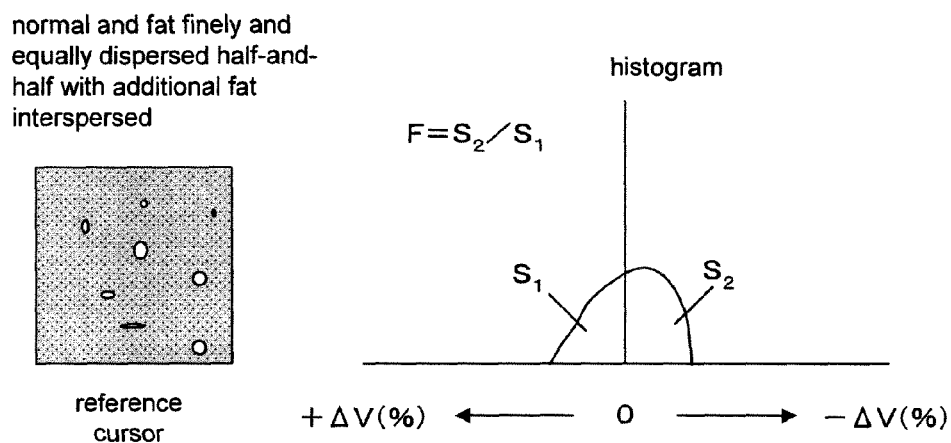
FIG. 8 is a diagram showing yet another example of a histogram in the case where a phantom is measured.

(4) In the Case Where Normal Regions and Fatty Regions Are Finely and Uniformly Dispersed Half-and-Half with Additional Fat Mixed In FIG. 8 shows a histogram in the case where a phantom, where fatty regions and normal regions are finely mixed with additional fat interspersed, is measured.

In this case, the histogram has an area $S_1$ and an area $S_2$ (here, $S_1$<S2), and a positive change in the velocity and a negative change in the velocity appear accordingly. The fatty change index F ($=S_2/S_1$) has a value slightly greater than 1.

Figure 9:
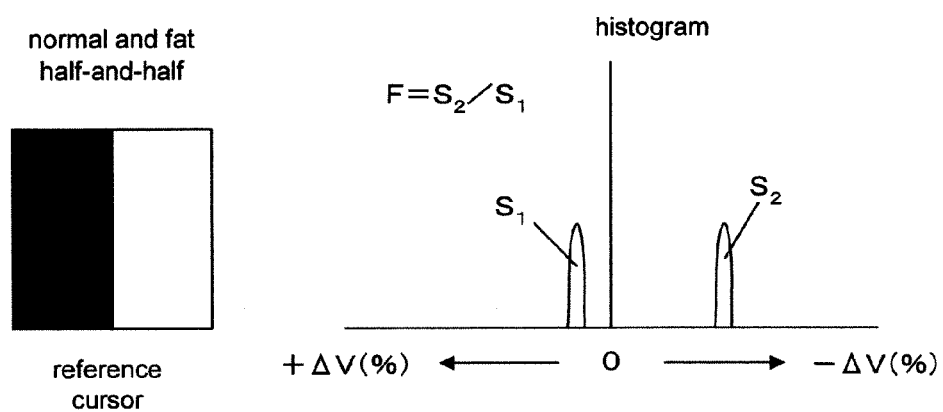
FIG. 9 is a diagram showing still yet another example of a histogram in the case where a phantom is measured.

(5) In the Case Where the Entirety is Divided Into Two Normal Region and Fatty Region FIG. 9 shows a histogram in the case where the region of interest (ROI) designated by the reference cursor is divided into two: a fatty region and a normal region. A rough marbled state is considered to be close to this state.

In this case, the histogram has an area $S_1$ for a positive change in the velocity and an area $S_2$ for a negative change in the velocity separated from each other. The fatty change index F ($=S_2/S_1$) has a value close to 1.

Figure 10:
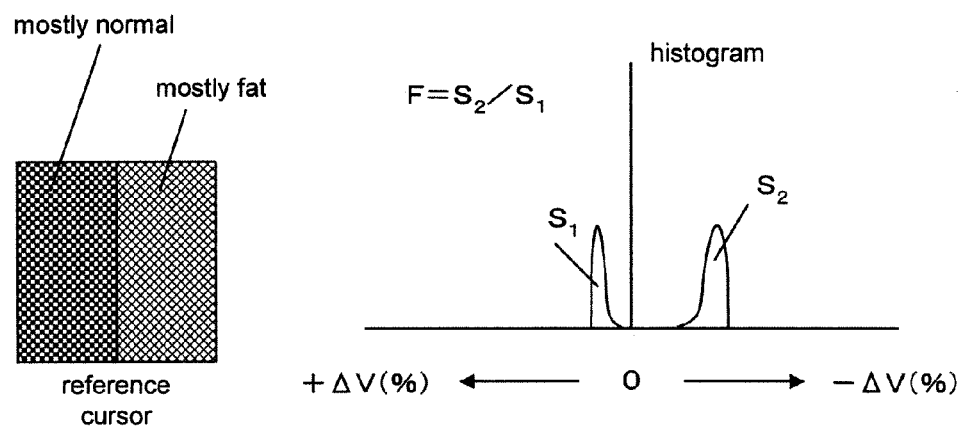
FIG. 10 is a diagram showing another example of a histogram in the case where a phantom is measured.

(6) In the Case Where the Entirety is Divided Into Two: Mostly Normal Region and Mostly Fatty Region FIG. 10 shows a histogram in the case where the region of interest (ROI) designated by the reference cursor is divided into two: a mostly fatty region and a mostly normal region. This is considered to be a slightly finer marbled state than a rough marbled state.

In this case, the histogram has an area $S_1$ for a positive change in the velocity and an area $S_2$ for a negative change in the velocity (here, $S_1$<$S_2$) separated from each other. The shape of the histogram is broader than in the above-described case (5). The fatty change index F ($=S_2/S_1$) has a value close to 1.

As can be analogically inferred from these phantoms, all the cases ranging from an extreme one consisting of only normal regions to an extreme one consisting of only fat can be expressed using a numerical value of the fatty change index F.

Though in the above-described examples the area ratio ($=S_2/S_1$) is used as the fatty change index F, alternatively, the fatty change index F=$\Sigma(Li \cdot S_2)/\Sigma(Mi \cdot S_1)$ where each level is weighted may be adopted.

(Display Examples of Line of Interest)

Figure 11:
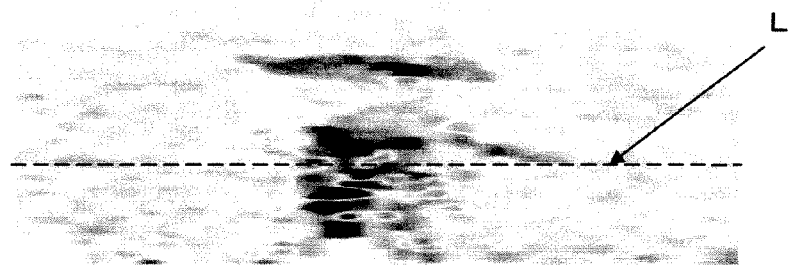
FIG. 11 is a photograph showing a screen for designating a line of interest.

Next, graphs showing the change in the velocity of the ultrasonic waves using a line of interest are described. FIG. 11 is a photograph showing a screen for designating a line of interest. When a starting point and an ending point of a line of interest are designated on the screen where an image of the change in the velocity of the ultrasonic waves is displayed, the line of interest L is displayed on the screen.

Figure 12:
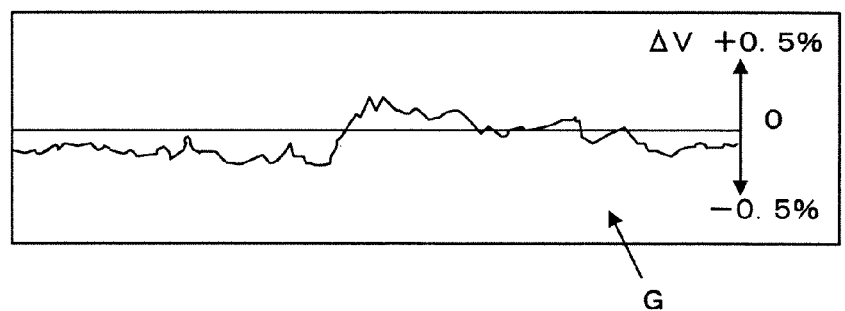
FIG. 12 is a graph showing the velocity of the ultrasonic waves at the points along a line of interest when the line is designated.
Figure 13:
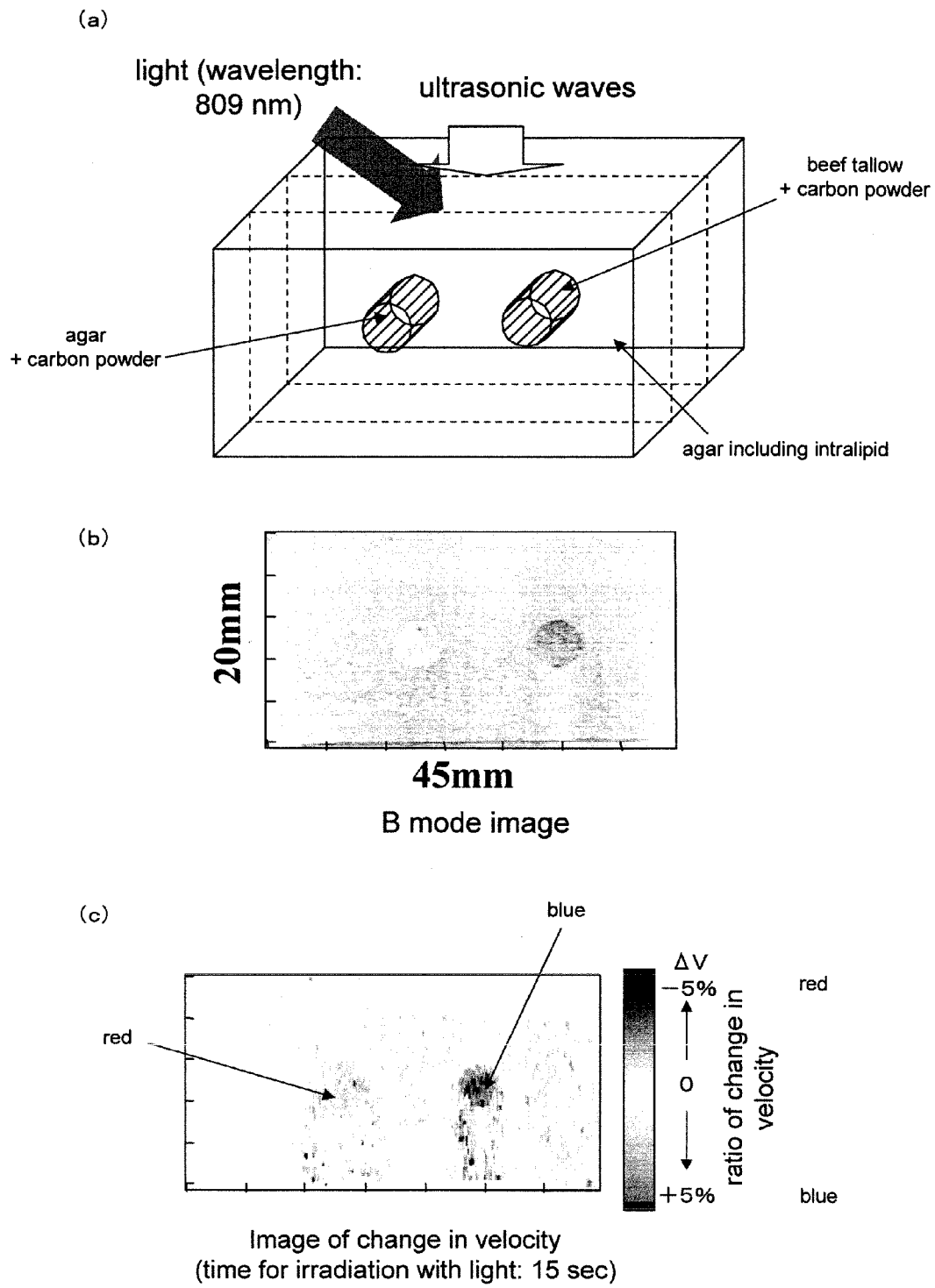
FIGS. 13(a) to 13(c) are diagrams showing an example of a tomographic image of fatty tissue.

Then, as shown in FIG. 12, the velocity of the ultrasonic waves at each point along the designated line is displayed in a graph G. In reference to this graph, the position of the reference cursor can be set because the degree of change in the velocity of the ultrasonic waves is easy to see in line form.

Though FIG. 11 shows only one line of interest, a number of lines may be displayed or a line of interest in the vertical direction (or diagonal direction) in addition to that in the horizontal direction may be displayed.

Furthermore, as another method for applying a line of interest, graphs displaying the change in the velocity of the ultrasonic waves along a line of interest in the same location may be periodically acquired for comparison. As a result, chronological changes in the fat content along a line of interest can be easily checked.

Though the embodiments of the present invention are described in the above, the present invention is not necessarily limited to these embodiments, and appropriate modifications and alterations are possible in order to achieve the object as long as the scope of the invention is not deviated from.

For example, the above-described embodiments use an infrared laser source as the heat source for heating a target portion. Instead of this, however, heating may be carried out using ultrasonic wave heating using an ultrasonic wave transmitter or electromagnetic wave heating, such as microwave heating.

INDUSTRIAL APPLICABILITY

The present invention can be applied to a fatty tissue image display device for imaging a fatty region for diagnosis.

EXPLANATION OF SYMBOLS

1: fatty tissue image display device
2: array transducer type probe
3: infrared laser source (heat source)
4: probe
5: transmission/reception unit
10: control system
11: digital scan converter (DSC) (image display control unit)
12: display device (liquid crystal panel)
13: input device
13a: keyboard
13b: mouse
21: irradiation control unit
22: scan control unit
23: B mode signal process
24: ultrasonic wave velocity change analysis unit
25: ultrasonic wave velocity change image display control unit
26: region-of-interest designation unit
26a: reference cursor
27: histogram calculation unit 28: fatty change index calculation unit
28a: area ratio
28b: weighted area ratio
29: line-of-interest designation unit
30: line-of-interest graph display control unit
100: subject
110: target portion

The invention claimed is:

1. A fatty tissue image display device, comprising:
a heater configured to heat a target region within a body;
an ultrasonic wave transmitter configured to transmit an ultrasonic wave signal to the target region;
an ultrasonic wave receiver configured to receive an ultrasonic wave echo signal from the target region; and
a computer device including a CPU and a memory, the computer device configured to:
  calculate a change in a velocity of the ultrasonic waves at each point within the target region before and after the target region is heated based on an ultrasonic wave echo signal received from the target region before the target region is heated and an ultrasonic wave echo signal received from the target region after the target region is heated;
display distribution of a calculated change in the velocity of the ultrasonic waves as a tomographic image on a screen of a display device, the distribution of the calculated change in the velocity of the ultrasonic waves being represented based on luminance information or color information;
designate part of said tomographic image as a region of interest;
calculate histograms of a fatty region showing a negative change in the velocity of the ultrasonic waves and a normal region showing a positive change in the velocity of the ultrasonic waves from the luminance information or color information within the designated region of interest; and
calculate a fatty change index that is an index of a proportion of fatty tissue from the histogram of the normal region only within the designated region of interest and the histogram of the fatty region within the designated region of interest, wherein
the computer device is further configured to
rank the luminance information or color information in multiple levels and display the ranked luminance information or color information on the screen when displaying the distribution of the calculated change in the velocity of the ultrasonic waves, and
calculate the fatty change index that is weighted based on the ranked luminance information or color information.

2. The fatty tissue image display device according to claim 1, wherein the computer device is configured to designate the region of interest with a reference cursor having a constant area.

3. The fatty tissue image display device according to claim 1, wherein the calculation of the fatty change index is to calculate a ratio of the total number of pixels for a positive change in the velocity to the total number of pixels for a negative change in the velocity in order to calculate the fatty change index.

4. The fatty tissue image display device according to claim 1, wherein the computer device is further configured to:
designate a location of a line of interest on a tomographic image; and
display as a graph the change in the velocity of the ultrasonic waves at each point along a designated line.

5. The fatty tissue image display device according to claim 1, wherein the heater is configured to generate one of a laser beam or an ultrasonic wave to heat the target region.

* * * * *